US012589095B2

(12) United States Patent
Wang

(10) Patent No.: US 12,589,095 B2
(45) Date of Patent: Mar. 31, 2026

(54) UNIT DOSAGE FORM FOR TRANSMUCOSAL DRUG DELIVERY OF AN ACTIVE PHARMACEUTICAL INGREDIENT

(71) Applicant: Primo Pharmatech LLC, Somerset, NJ (US)

(72) Inventor: Zheng Wang, Bridgewater, NJ (US)

(73) Assignee: PRIMO PHARMATECH LLC, Somerset, NJ (US)

( * ) Notice: Subject to any disclaimer, the term of this patent is extended or adjusted under 35 U.S.C. 154(b) by 626 days.

(21) Appl. No.: 17/610,965

(22) PCT Filed: May 29, 2020

(86) PCT No.: PCT/US2020/035273

§ 371 (c)(1),
(2) Date: Nov. 12, 2021

(87) PCT Pub. No.: WO2020/243538

PCT Pub. Date: Dec. 3, 2020

(65) Prior Publication Data

US 2022/0249465 A1 Aug. 11, 2022

Related U.S. Application Data

(60) Provisional application No. 62/855,319, filed on May 31, 2019.

(51) Int. Cl.

| | |
|---|---|
| ***A61K 38/095*** | (2019.01) |
| ***A61K 9/00*** | (2006.01) |
| ***A61K 31/397*** | (2006.01) |
| ***A61K 31/4045*** | (2006.01) |
| ***A61K 31/4178*** | (2006.01) |
| ***A61K 31/4196*** | (2006.01) |
| ***A61K 31/445*** | (2006.01) |
| ***A61K 31/47*** | (2006.01) |
| ***A61K 31/485*** | (2006.01) |
| ***A61K 31/4985*** | (2006.01) |
| ***A61K 31/522*** | (2006.01) |
| ***A61K 38/12*** | (2006.01) |
| ***A61K 38/58*** | (2006.01) |
| ***A61K 47/02*** | (2006.01) |
| ***A61K 47/10*** | (2017.01) |
| ***A61K 47/12*** | (2006.01) |
| ***A61K 47/18*** | (2017.01) |
| ***A61K 47/26*** | (2006.01) |

(52) U.S. Cl.

CPC ............ *A61K 31/485* (2013.01); *A61K 9/006* (2013.01); *A61K 31/397* (2013.01); *A61K 31/4045* (2013.01); *A61K 31/4178* (2013.01); *A61K 31/4196* (2013.01); *A61K 31/445* (2013.01); *A61K 31/47* (2013.01); *A61K 31/4985* (2013.01); *A61K 31/522* (2013.01); *A61K 38/095* (2019.01); *A61K 38/12* (2013.01); *A61K 38/58* (2013.01); *A61K 47/02* (2013.01); *A61K 47/10* (2013.01); *A61K 47/12* (2013.01); *A61K 47/183* (2013.01); *A61K 47/26* (2013.01)

(58) Field of Classification Search

None

See application file for complete search history.

(56) References Cited

U.S. PATENT DOCUMENTS

| | | | | |
|---|---|---|---|---|
| 284,464 A * | 9/1883 | Michaelis | A23G 3/54 | 426/103 |
| 6,350,470 B1 * | 2/2002 | Pather | A61K 9/2886 | 514/960 |
| 2001/0014658 A1 * | 8/2001 | Smith | C11D 1/722 | 510/421 |
| 2003/0077297 A1 | 4/2003 | Chen et al. | | |
| 2004/0248846 A1 * | 12/2004 | Quay | A61K 9/1075 | 514/419 |
| 2005/0260323 A1 * | 11/2005 | Sperling | A23L 2/54 | 426/590 |
| 2006/0003989 A1 * | 1/2006 | Quay | A61K 45/06 | 514/214.03 |
| 2007/0299121 A1 * | 12/2007 | Huhtinen | A61P 25/22 | 514/396 |
| 2008/0152597 A1 | 6/2008 | Reed et al. | | |
| 2009/0074859 A1 | 3/2009 | Patel | | |
| 2009/0143390 A1 | 6/2009 | Cincotta | | |
| 2009/0163447 A1 | 6/2009 | Maggio | | |

(Continued)

FOREIGN PATENT DOCUMENTS

| | | |
|---|---|---|
| CN | 1271276 A | 10/2000 |
| CN | 1414853 A | 4/2003 |

(Continued)

OTHER PUBLICATIONS

Casiraghi A, Di Grigoli M, Cilurzo F, Gennari CG, Rossoni G, Minghetti P. The influence of the polar head and the hydrophobic chain on the skin penetration enhancement effect of poly(ethylene glycol) derivatives. AAPS PharmSciTech. Mar. 2012;13(1):247-53. doi: 10.1208/s12249-011-9745-4. (Year: 2012).*

(Continued)

*Primary Examiner* — Ali Soroush
*Assistant Examiner* — Afua Bamfoaa Boateng
(74) *Attorney, Agent, or Firm* — FOX ROTHSCHILD LLP

(57) ABSTRACT

A novel unit dosage form for oral transmucosal delivery of an active pharmaceutical ingredient (API). The dosage form contains a permeation enhancer that promotes fast absorption, rapid onset of action, and overall high bio availability for the API.

6 Claims, 2 Drawing Sheets

(56) References Cited

U.S. PATENT DOCUMENTS

| | | | | |
|---|---|---|---|---|
| 2012/0009260 | A1* | 1/2012 | Schobel | A61K 9/006 514/12.3 |
| 2014/0128422 | A1 | 5/2014 | Dey et al. | |
| 2014/0249136 | A1* | 9/2014 | Cincotta | A61K 9/06 514/250 |
| 2016/0235764 | A1 | 8/2016 | Ahmed et al. | |

FOREIGN PATENT DOCUMENTS

| | | | |
|---|---|---|---|
| CN | 101674843 | A | 3/2010 |
| CN | 107441065 | A | 12/2017 |
| CN | 108366961 | A | 8/2018 |

OTHER PUBLICATIONS

Avena Lab "Decyl Oleate", Sep. 14, 2020, Retrieved from https://www.avenalab.com/sirovina/emolijensi/specijalni-emolijensi/decyloleate-detail, entire document especially p. 2, Para 7.

Chaomei et al: "Pharmaceutical Excipients", China University of Traditional Chinese Medicine Press, Oct. 2008, ISBN 978-7-80231-461-0.

Wang Xiaobo: "Drug Delivery System", China Medical Science and Technology Press, Aug. 2007, ISBN 978-7-5067-3732-6.

Avena Lab: "Decyl Oleate", Sep. 14, 2020, Retrieved from the Internet: <URL: https://www.avenalab.com/sirovine/emolijensi/specijalni-emolijensi/decyloleate-detail, entire document especially p. 2, Para 7.

* cited by examiner

UNIT DOSAGE FORM FOR TRANSMUCOSAL DRUG DELIVERY OF AN ACTIVE PHARMACEUTICAL INGREDIENT

CROSS-REFERENCE TO RELATED APPLICATIONS

The present application is the U.S. National Phase of International Patent Application Serial No. PCT/US20/35273, filed May 29, 2020, which claims priority under 35 U.S.C. § 119(e) to U.S. Provisional Patent Application Ser. No. 62/855,319, filed on May 31, 2019. The entire disclosures of the applications noted above are incorporated herein by reference.

TECHNICAL FIELD

Disclosed herein is a novel unit dosage form for oral transmucosal delivery of a therapeutic agent.

BACKGROUND

The oral administration of medicaments to both pediatric and adult patient populations can often be a challenge. Particularly, patients are often reluctant to swallow pills, tablets, capsules, or other solid dosage medicament formulations, especially when the act of swallowing is problematic for that individual. For example, global hystericus and choking due to pharyngeal and esophageal motility problems, renders it painful to swallow and often results in aversion to swallowing the formulation. In addition, patients with pharyngitis and/or a markedly swollen or an otherwise severely irritated pharynx, such as due to a bacterial infection, often makes it difficult and/or impossible for the patient to swallow a solid medicament formulation. Patients may also be reluctant to ingest a medicament formulation due to its size, shape, and taste, psychological aversion to the act of ingestion, and/or personal choice not to swallow the formulation. However, patients under a medication regimen and/or in need of the therapeutic active ingredient in the formulation must self-administer, or be administered, the dose.

For instance, many patients having Parkinson's disease develop involuntary choreiform movements which are the result of excessive activation of dopamine receptors. These movements usually affect the face and limbs and can become very severe. Such movements disappear if the dose of dopamine precursor (e.g., levodopa) or dopamine agonist is reduced, but this typically causes rigidity to return. Moreover, the margin between the beneficial and the unwanted effects appear to become progressively narrower as the period of chemotherapeutic treatment lengthens. Conventional pharmaceutical formulations do not address the problems associated with these patients who are averted to, or otherwise have difficulty with, swallowing the same.

Accordingly, there is a need to deliver a medicament to a patient in a convenient and effective manner There is also a need to improve patient compliance with ingestion of a medicament. There is also a need to deliver the medicament in a formulation suitable for administration to patients who are otherwise averted to and/or not able to swallow. There is yet a further need to provide a method of delivering pharmaceutical medicaments to patients in an inexpensive, patient-friendly manner, while addressing the drawbacks and weaknesses associated with traditional methods of administering medicaments.

SUMMARY

An aspect of this patent document provides a unit dosage form formulated for oral transmucosal delivery of an active pharmaceutical ingredient (API). The dosage form includes a therapeutically effective amount of the API, and a permeation enhancer. The permeation enhancer is in an effective amount to enable the API of the unit dosage form to reach a permeability coefficient of at least 1.25 cm/h as measured by the Franz Cell System using 0.45 μm Nylon as penetration media. The permeation enhancer contains at least one of the following: (a) at least an ester of a fatty acid, wherein the permeation enhancer has a HLB value ranging from about 8 to about 10; and (b) a gas-producing component. In some embodiments, the derived ester of a fatty acid is an oleic acid derived surfactant. The ester can be prepared for example with PEG or glycerol.

In some embodiments, the API is selected from the group consisting of montelukast, tadalafil, apomorphine, small peptides, preferably with less than 20 amino acids, including bivalirudin, octreotide, desmopressin, oxytocin, atosiban, as well as ondansetron, rizatriptan, donepezil, loperamide, Ezetimibe, melatonin and caffeine. In some embodiments, the API is apomorphine ranging from about 5 mg to about 40 mg.

In some embodiments, the permeation enhancer comprises at least one of PEG-6 mono-oleate and PEG-6 di-oleate. In some embodiments, the permeation enhancer further includes at least one of glycerol mono-oleate, glycerol di-oleate, and glycerol mono-oleate, and glycerol tri-oleate. In some embodiments, the permeation enhancer consists essentially of at least one of PEG-6 mono-oleate and PEG-6 di-oleate, and at least one of glycerol mono-oleate, glycerol di-oleate, glycerol tri-oleate, oleic acid, sorbitan monooleate and polyoxytheylene sorbitan monooleate. In some embodiments, the at least one of PEG-6 mono-oleate and PEG-6 di-oleate weighs more than about 30% in the permeation enhancer. the PEG-6 mono-oleate weighs less than about 80% in the permeation enhancer.

In some embodiments, the API and the permeation enhancer is in a ratio ranging from about 100:1 to about 1:5. In some embodiments, the API and the permeation enhancer are in a single layer film. In some embodiments, the permeation enhancer further comprises a gas-producing component. In some embodiments, the gas-producing component comprises particles containing pressured gas of more than about 300 psi. In some embodiments, the gas-producing component comprises an acid and a carbonate or bi-carbonate agent, and the acid and the carbonate or bi-carbonate agent are disposed in two separate layers. In some embodiments, the acid comprises citric acid and the carbonate comprises sodium bicarbonate. In some embodiments, the acid and the carbonate or bi-carbonate agent are in a ratio of about 1:3.

Another aspect of the document provides a method of treating a disease in a subject, comprising administrating the unit dosage form described herein. Non-limiting examples of the disease include Parkinson's disease, erectile dysfunction, Alzheimer's disease, asthma, diarrhea, and migraine headache.

In some embodiments, the method further includes administering a second agent selected from the group consisting of antihistamines, medications treat respiratory disorders, antiemetics, sleep aids, medications to treat diarrhea, oral hygiene agents, migraine treatments, CNS medicines, and first-aid medications.

DETAILED DESCRIPTION

Figure 1:
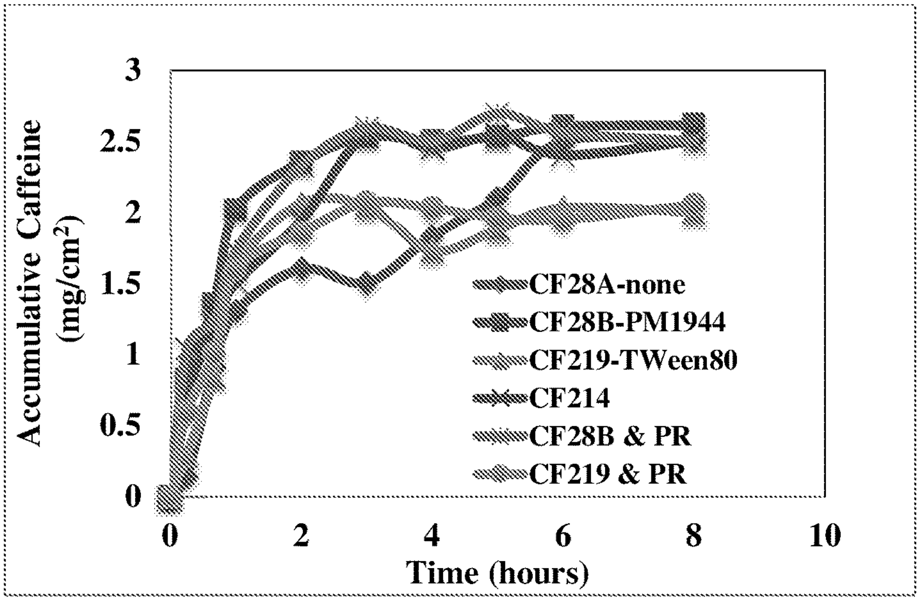
FIG. 1 illustrates in vitro release of caffein from an exemplified oral thin film over a period of 9 hours.

The unit dosage form of this patent document is suitable for oral mucosae delivery of pharmaceutically active ingredient (API) or a therapeutical agent. The API is formulated for fast uptake through sublingual, buccal and gingiva delivery. Furthermore, the convenience with which the dosage form can be self administered provides a significant advantage to severely patients with compromised motor skills.

While the following text may reference or exemplify specific embodiments of a dosage form or a method of treating a disease or condition, it is not intended to limit the scope of the dosage form or method to such particular reference or examples. Various modifications may be made by those skilled in the art, in view of practical and economic considerations, such as the excipient of the formulation and the amount or administration of the API for treating a disease or condition.

The articles "a" and "an" as used herein refers to "one or more" or "at least one," unless otherwise indicated. That is, reference to any element or component of an embodiment by the indefinite article "a" or "an" does not exclude the possibility that more than one element or component is present.

The term "active pharmaceutical ingredient" (API) as used herein refers to a compound or an agent that provides a therapeutic effect for treating a disease or a condition in a subject.

The term "effervescence" as used herein refers to the escape of a gas from a liquid or mixture. Thus, the effervescent component or gas-producing component as used herein, is intended to generally refer to a component or a mixture of components that evolve one or more gases, under proper conditions, such as upon contact with water.

The term "carrier" refers to a chemical compound that facilitates the incorporation of a compound into cells or tissues.

The term "diluent" refers to chemical compounds diluted in water that will dissolve the composition of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. As used herein, an "excipient" refers to an inert substance that is added to a composition to provide, without limitation, bulk, consistency, stability, binding ability, lubrication, disintegrating ability, etc., to the composition. A "diluent" is a type of excipient.

The term "film" as used herein includes thin films, sheets and wafers, in any shape, including rectangular, square, or other desired shape. The films described herein may be any desired thickness and size such that it may be placed into the oral cavity of the user. For example, the films may have a relatively thin thickness of from about 0.1 to about 10 millimeters, or they may have a somewhat thicker thickness of from about 10 to about 30 millimeters. For some films, the thickness may be even larger, i.e., greater than about 30 millimeters. Films may be in a single layer or they may be multi-layered, including laminated films.

The term "physiologically acceptable" or "pharmaceutically acceptable" refers to a carrier or diluent that does not abrogate the biological activity and properties of the compound.

The term "subject" refers to as a human or an animal

The term "effective amount" or "therapeutically effective amount" refers to an amount of a compound effective to inhibit bacterial growth, or prevent, alleviate or ameliorate symptoms of disease or prolong the survival of the subject being treated. Determination of a therapeutically effective amount is well within the capability of those skilled in the art, especially in light of the detailed disclosure provided herein.

The term "oral transmucosal delivery" refers to the uptake of an API through sublingual mucosa and/or buccal mucosa. Oral mucosa includes sublingual mucosa and buccal mucosa.

The term "treating" or "treatment" of any disease or condition refers, in some embodiments, to ameliorating the disease or disorder (i.e., arresting or reducing the development of the disease or at least one of the clinical symptoms thereof). In some embodiments "treating" or "treatment" refers to ameliorating at least one physical parameter, which may not be discernible by the subject. In some embodiments, "treating" or "treatment" refers to modulating the disease or disorder, either physically, (e.g., stabilization of a discernible symptom), physiologically, (e.g., stabilization of a physical parameter), or both. In some embodiments, "treating" or "treatment" refers to delaying the onset of the disease or disorder, or even preventing the same. "Prophylactic treatment" is to be construed as any mode of treatment that is used to prevent progression of the disease or is used for precautionary purpose for persons at risk of developing the condition.

An aspect of this patent document provides a unit dosage form formulated for oral transmucosal delivery of an active pharmaceutical ingredient (API). The unit dosage form includes an API, and a primary permeation enhancer. The primary permeation enhancer contains one or both of a PEG derived ester of a fatty acid and a gas-producing component. In some embodiments, the permeation enhancer is in an effective amount to enable the API (e.g. caffeine) of the unit dosage form to reach a permeability coefficient of at least 0.8, at least 1.0, at least 1.25, at least 1.50, or at least 1.75 cm/h as measured by the Franz Cell System using 0.45 μm Nylon as penetration media.

In some embodiments, the primary permeation enhancer has at least a PEG derived ester of a fatty acid with a hydrophilic-lipophilic balance (HLB) value ranging from about 4.3 to about 16. In some embodiments, the HLB value ranges from about 7 to about 11, from about 9 to about 11, from about 8 to about 11, from about 8 to about 10, from about 8 to about 9, or from about 9 to about 10. In some embodiments, the primary permeation enhancer has a gas producing component.

Because of the thin membrane and rich blood supply in the sublingual and buccal mucosa, the oral transmucosal delivery provides fast absorption, a rapid onset of action, and overall high bioavailability of an API. In some embodiments, more than about 20%, more than about 30%, more than about 40%, more than about 50%, more than about 60%, more than about 70%, more than about 80%, more than about 90%, or substantially all of the API in the unit dosage form is absorbed through the sublingual and buccal mucosa.

The unit dosage form may be in any suitable form including for example, an oral dispersible pill, a chewable pill, a buccal adhesive pill, a tablet, a capsule, a granular powder, a troche, a dragée, a buccal adhesive pill, and a film. The formulations may be multi-layered to optimize disintegration of the formulation, and/or dispersion of the API or medicament, in the vehicle. The formulations may also be of varied shape, such as a biconcave shaped tablet to improve disintegration of the formulation and dispersion of the medicament in the vehicle. The formulation should also be substantially anhydrous to increase storage stability. In some embodiments, the unit dosage form is a multi-layered (e.g. 2, 3, or 4) film. In some embodiments, the unit dosage form is a single-layered film.

In some embodiments, the API is selected from the group consisting of montelukast, tadalafil, apomorphine, small peptides, preferably with less than 20 amino acids, including bivalirudin, octreotide, desmopressin, oxytocin, atosiban, as well as ondansetron, rizatriptan, donepezil, loperamide, Ezetimibe, melatonin and caffeine. In some embodiments, the API is apomorphine or a pharmaceutically acceptable salt thereof. In some embodiments, the API is the hydrochloride salt of apomorphine. In some embodiments, the unit dosage form includes a second therapeutic agent. Non-limiting examples include antihistamines, medications treating respiratory disorders, antiemetics, sleep aids, medications to treat diarrhea, oral hygiene agents, migraine treatment medications, CNS medicines, and first-aid medications.

The ration by weight between the API and the permeation enhancer ranges from about 100:1 to about 1:10. In some exemplary embodiments, the ratio ranges from about 50:1 to about 1:5, from about 20:1 to about 1:5, from about 10:1 to about 1:5, from about 10:1 to about 1:2, from about 10:1 to about 1:1, from about 10:1 to about 2:1, from about 10:1 to about 3:1, from about 7:1 to about 1:5, from about 7:1 to about 1:2, from about 7:1 to about 1:1, from about 7:1 to about 2:1, from about 7:1 to about 3:1, from about 5:1 to about 1:5, from about 5:1 to about 1:2, from about 5:1 to about 1:1, from about 5:1 to about 2:1, or from about 5:1 to about 3:1.

The amount of API in the unit dosage form may vary depends on the specific agent, expients and disease to be treated. In some embodiemnts, the API ranges from about 0.1 mg to about 100 mg. In some embodiments, the API in the unit dosage form ranges from about 0.1 mg to about 50 mg, from about 0.5 mg to about 50 mg, from about 1 mg to about 50 mg, from about 1 mg to about 40 mg, from about 1 mg to about 30 mg, from about 1 mg to about 20 mg, from about 1 mg to about 10 mg, from about 1 mg to about 5 mg, from about 2 mg to about 30 mg, from about 2 mg to about 20 mg, from about 2 mg to about 10 mg, from about 2 mg to about 5 mg, from about 5 mg to about 30 mg, from about 5 mg to about 20 mg, or from about 5 mg to about 10 mg.

In some embodiments, the API accounts for about 1% to about 70%, about 1% to about 50%, about 1% to about 40%, about 1% to about 30%, about 1% to about 20%, about 1% to about 10%, about 5% to about 50%, about 5% to about 40%, about 5% to about 30%, about 5% to about 20%, about 5% to about 10%, about 10% to about 20%, or about 10% to about 15% of the total weight of the unit dosage form.

The primary permeation enhancer contains one or more ester forms of a fatty acid. Non-limiting examples of the ester forms include a PEG derived mono-ester, a PEG derived di-ester, a glycerol-derived mono-ester (e.g. 1-monoacylglycerol), a glycerol-derived di-ester (e.g. 1,2-diacylglycerol, 1,3-diacylglycerol), and a glycerol-derived tri-ester (e.g. triacylglycerol). In some embodiments, the primary permeation enhancer serves to modulate the rate of mucosal absorption of the API, and is in an effective amount such that the API of the unit dosage form reaches a permeability coefficient of at least 1.25 cm/h as measured by the Franz Cell system using the 0.45 micron Nylon Filter as the penetration medium. Non-limiting examples of the fatty acid includes caprylic acid, capric acid, lauric acid, myristic acid, palmitic acid, stearic acid, oleic acid, ricinoleic acid, linolenic acid, eicosenoic acid, behenic acid, and erucic acid.

In some embodiments, the primary permeation enhancer contains one or both of a PEG derived mono-ester of a fatty acid and PEG derived di-ester of a fatty acid. As illustrated below, each RCOO derives from a fatty acid. Each R in the formula can be the same or different. The subscript n is an integer which can be for example 2, 3, 4, 5, 6, 7, 8, 9, 10, or a greater number.

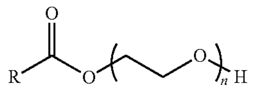

PEG derived mono-ester

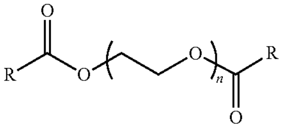

PEG derived di-ester

In some embodiments, the fatty acid is oleic acid. Non-limiting examples of PEG derived esters of a fatty acid include polyooxyglycerides such as PEG-6 mono-oleate and PEG-6 di-oleate. In some embodiments, the primary permeation enhancer comprises at least one of PEG-6 mono-oleate and PEG-6 di-oleate, and at least one of glycerol mono-oleate, glycerol di-oleate, and glycerol mono-oleate, and glycerol tri-oleate. In some embodiments, the primary permeation enhancer consists essentially of at least one of PEG-6 mono-oleate and PEG-6 di-oleate, and at least one of glycerol mono-oleate, glycerol di-oleate, and glycerol mono-oleate, and glycerol tri-oleate.

In some embodiments, the primary permeation enhancer further contains at least one of glycerol mono-ester of a fatty acid (or monoacylglyceride such as 1-monoacylglycerol and 3-monoacylglycerol), glycerol di-ester of a fatty acid (or diacylglyceride such as 1,2-diacylglycerol and 1,3-diacylglycerol), and glycerol tri-ester of a fatty acid (or triglyceride or triacylglycerol). In some embodiments, the fatty acid is oleic acid.

The HLB value of the primary permeation enhancer needs to be controlled in a suitable range to facilitate the mucosae permeation of the API. Accordingly, the ratio among the individual components of the permeation enhancer should be adjusted to achieve a suitable balance of lipophilicity and hydrophilicity.

In some embodiments, the primary permeation enhancer consists essentially of at least one of PEG-6 mono-oleate and PEG-6 di-oleate, and at least one of glycerol mono-oleate, glycerol di-oleate, and glycerol mono-oleate, and glycerol tri-oleate. Meanwhile, the total of PEG-6 mono-oleate and PEG-6 di-oleate accounts for more than about 20%, more than about 25%, more than about 30%, more than about 35%, more than about 40%, more than about 45%, more than about 50%, more than about 55%, more than about 60%, more than about 65%, more than about 70%, more than about 75%, more than about 80%, more than about 85%, more than about 90%, or more than about 95%, more than about 99% by weight of the primary permeation enhancer. In some embodiments, the amount of the PEG-6 mono-oleate is less than about 90%, less than about 85%, less than about 80%, less than about 75%, or less than about 70% by weight of the primary permeation enhancer. In some embodiments, the total of PEG-6 mono-oleate and PEG-6 di-oleate accounts for more than about 30% by weight of the primary permeation enhancer, and the PEG-6 mono-oleate is less than about 80% by weight of the primary permeation enhancer. In some embodiment, the primary permeation enhancer is the only permeation enhancer in the unit dosage form. In some embodiments, the HLB of the primary permeation enhancer ranges from about 7 to about 11, from about 9 to about 11, from about 8 to about 11, or from about 8 to about 10.

In some embodiments, the primary permeation enhancer consists essentially of one or both of PEG-6 mono-oleate and PEG-6 di-oleate, and one, two or three of glycerol mono-oleate, glycerol di-oleate, and glycerol tri-oleate. In some embodiments, the primary permeation enhancer consists essentially of PEG-6 mono-oleate and PEG-6 di-oleate. In some embodiments, the primary permeation enhancer consists essentially of PEG-6 mono-oleate, PEG-6 di-oleate, glycerol mono-oleate, glycerol di-oleate, and glycerol tri-oleate. In some embodiments, the primary permeation enhancer consists essentially of PEG-6 mono-oleate and glycerol tri-oleate. In some embodiments, the primary permeation enhancer consists essentially of PEG-6 mono-oleate and glycerol mono-oleate. In some embodiments, the primary permeation enhancer consists essentially of PEG-6 mono-oleate, PEG-6 di-oleate, and glycerol mono-oleate. In some embodiments, the primary permeation enhancer consists essentially of PEG-6 mono-oleate, PEG-6 di-oleate, glycerol mono-oleate, and glycerol di-oleate. In some embodiments, the HLB of the primary permeation enhancer ranges from about 7 to about 11, from about 9 to about 11, from about 8 to about 9, from about 9 to about 10, or from about 8 to about 10.

In some embodiments, the amount of the PEG-6 mono-oleate can ranges from about 15% to about 25%, from about 25% to about 35%, from about 30% to about 40%, from about 40% to about 50%, from about 50% to about 60%, from about 60% to about 70%, from about 70% to about 80%, or from about 80% to about 90% by weight in the primary permeation enhancer. In some embodiments, the amount of the PEG-6 di-oleate can ranges from about 0% to about 5%, from about 5% to about 10%, from about 10% to about 15%, from about 15% to about 25%, from about 25% to about 35%, from about 30% to about 40%, from about 40% to about 50%, from about 50% to about 60%, from about 60% to about 70%, from about 70% to about 80%, or from about 80% to about 90% by weight in the primary permeation enhancer. In some embodiments, the amount of the glycerol mono-oleate, can ranges from about 0% to about 5%, from about 5% to about 10%, from about 10% to about 15%, from about 15% to about 25%, from about 25% to about 35%, from about 30% to about 40%, from about 40% to about 50%, from about 50% to about 60%, from about 60% to about 70%, from about 70% to about 80%, or from about 80% to about 90% by weight in the primary permeation enhancer. In some embodiments, the amount of the glycerol di-oleate, can ranges from about 0% to about 5%, from about 5% to about 10%, from about 10% to about 15%, from about 15% to about 25%, from about 25% to about 35%, from about 30% to about 40%, from about 40% to about 50%, from about 50% to about 60%, from about 60% to about 70%, from about 70% to about 80%, or from about 80% to about 90% by weight in the primary permeation enhancer. In some embodiments, the amount of the glycerol tri-oleate, can ranges from about 0% to about 5%, from about 5% to about 10%, from about 10% to about 15%, from about 15% to about 25%, from about 25% to about 35%, from about 30% to about 40%, from about 40% to about 50%, from about 50% to about 60%, from about 60% to about 70%, from about 70% to about 80%, or from about 80% to about 90% by weight in the primary permeation enhancer. In some embodiments, the HLB of the primary permeation enhancer ranges from about 7 to about 11, from about 8 to about 9, from about 9 to about 10, from about 8 to about 10.

In some embodiments, the primary permeation enhancer contains one or both of PEG-6 mono-oleate and PEG-6 di-oleate, and the one or both of PEG-6 mono-oleate and PEG-6 di-oleate weighs more than about 20%, more than about 30%, more than about 40%, more than about 50%, more than about 60%, or more than about 70% in the primary permeation enhancer. In some embodiments, the amount of PEG-6 mono-oleate is less than about 90%, less than about 80%, less than about 70%, less than about 60% in the primary permeation enhancer. As stated above, in some embodiments, the HLB of the primary permeation enhancer ranges from about 7 to about 11, from about 8 to about 9, from about 9 to about 10, from about 8 to about 10.

Other agents can also be included in the dosage form as a secondary or additional permeation enhancer. Examples of additional permeation enhancer includes bile salts, such as sodium cholate, sodium glycocholate, sodium glycodeoxycholate, taurodeoxycholate, sodium deoxycholate, sodium lithocholate chenocholate, chenodeoxycholate, ursocholate, ursodeoxy-cholate, hyodeoxycholate, dehydrocholate, glycochenocholate, taurochenocholate, and taurochenodeoxycholate; sodium dodecyl sulfate (SDS), dimethyl sulfoxide (DMSO), N-lauroyl sacrcosine, sorbitan monolaurate, stearyl methacrylate, N-dodecylazacycloheptan-2-one, N-dodecyl-2-pyrrolidinone, N-dodecyl-2-piperidinone, 2-(1-nonyl)-1,3-dioxolane, N-(2-methoxymethyl) dodecylamine, N-dodecylethanolamine, N-dodecyl-N-(2-methoxymethyl)acetamide, 1-N-dodecyl-2-pyrrolidone-5-carboxylic acid, 2-pentyl-2-oxo-pyrrolidineacetic acid, 2-dodecyl-2-oxo-l-pyrrolidineacetic acid, 2-dodecyl-2-oxo-1-pyrrolidineacetic acid, 1-azacylioheptan-2-one-dodecylacetic acid, menthol, propylene glycol, glycerol monostearate, sorbitol monolaurate, glycerol dilaurate, tocopherol acetate, phosphatidyl choline, glycerol, polyethyleneglycol, lecithin, tween surfactants, sorbitan surfactants, sodium lauryl sulfate; oleic acid, sorbitan monooleate and polyoxytheylene sorbitan monooleate; salts and other derivatives of saturated and unsaturated fatty acids, surfactants, bile salt analogs, derivatives of bile salts, or such synthetic permeation enhancers as described in U.S. Pat. No. 4,746,508, which is incorporated herein by reference.

In some embodiments, the permeation enhancer accounts for about 0.5% to about 50%, about 0.5% to about 40%, about 0.5% to about 30%, about 0.5% to about 20%, about 0.5% to about 10%, about 0.5% to about 8%, about 0.5% to about 5%, about 0.5% to about 2%, about 0.5% to about 1%, about 1% to about 30%, about 1% to about 20%, about 1% to about 10%, about 1% to about 5%, about 1% to about 3%, about 5% to about 30%, about 5% to about 20%, or about 5% to about 10% of the total weight of the unit dosage form.

The unit dosage form can include a gas-producing component to facilitate permeation of the API. The cells of the oral mucosae are bound together by small structures called desmosomes with a tight junction space of approximately 20 nm between adjacent cells. Without being bound by any particular theory, it is believed that the impact of gas may stimulate blood circulation in oral mucosae and open up the tight junction for increased uptake of API. Accordingly, the gas-producing component can be incorporated into the unit dosage form, alone or in combination with the above described primary permeation enhancer and/or secondary permeation enhancer agent, to promote transmucosal delivery of API.

In some embodiments, the gas-producing component is a particle encapsulating or trapping pressured gas. The pressured gas may have a pressure of more than about 50, more than about 100, more than about 200, more than about 300, more than about 400, more than about 500, or more than about 600 psi.

In an exemplary embodiment for the preparation of the gas-producing component, the process includes: gasifying a fused fusible excipient or substrate (e.g. sugar) at superatmospheric pressure and cooling the gasified fused fusible excipient or substrate below its fusion temperature under the gasifying pressure thereby forming a gasified solid containing therewithin a gas under superatmospheric pressure. The gasifying can be effected with a gas such as carbon dioxide, nitrogen, helium, and air.

The gases included in the gas-producing component should be pharmaceutically acceptable, as they may or may not be ingested with the formulation. For example, inert gases including, without limitation, carbon dioxide, nitrogen, air, helium, ethylene oxide, oxygen, and combinations thereof, are suitable. Suitable gas-producing components and methods of making same are described in U.S. Pat. No. 3,012,893, which disclosure is incorporated herein by reference in its entirety. Suitable gasified solids that are stable at room temperature and soluble in minimal amounts of water, or in nearly anhydrous or oligohydrous vehicles, are also described in U.S. Pat. No. 6,364,521, which disclosures are incorporated herein by reference in their entireties. These patents also describe the formulation and manufacture of gasified solid matrices, including gasified sugars.

The amount of the gas-producing component ranges from about 5% to about 90%, from about 15% to about 80%, from about 25% to about 60%, or from about 35% to about 50% of the total weight of the unit dosage form. In some embodiments, the gas-producing component is an aqueous dissolvable solid matrix having one or more first gases contained therein. Suitable gas-producing components may be produced by dispersing the gas within a liquid, molten sugar, or other suitably dispersing liquid or medium, and then solidifying the dispersing medium to form a bubble, which contains or "entraps" the gas therein. The resulting gas-dispersing component is generally referred to as a "solid foam". Suitable media for the aqueous dissolvable solid matrix includes, without limitation, carbohydrates, monosaccharides, di-saccharides, poly-saccharides of simple sugars, sugar derivatives, and the like. Examples of suitable materials for forming the gas-dispersing component include, without limitation, high caloric sugars such as sucrose, lactose, glucose, d-glucose, I-glucose, maltose, dextrose, fructose, fructosan, gentiobiose, cellobiose, panose, maltotriose, malto-tetrose, arabinose, mannose, d-mannose, galactose, d-galactose, d-glyceraldehyde, amylose, allose, altose, talose, gulose, idose, ribose, erythrose, threose, lyxose, xylose, d-xylose, rhamnose, invert sugar, corn sugar, inositol, glycerol, glycogen, pectin, agar, sorbitol, mannitol and combinations thereof; low caloric sugars, such as sucralose, polyols, tagarose, trehalose, xylitol, dextrans, dextrins, dextrates, polysorbates, maltodextrin, xylitol, amylase, amylopectin, ribose, β-maltose, fucose, sialic acid (neuraminic acid), N-acetylgalactosamine, N-acetylglucosamine, sedoheptulose, ribulose, xylulose and combinations thereof; non-sugar sweeteners, such as acesulfane potassium, aspartame, neotame, saccharin, stevioside and combinations thereof; non-sweeteners, such as alitame, cyclamate, dihydrochalcones (DHCs), glycyrrhizin, thaumatin, gelatin, glycerin, triacetin, trehalose, alginates, gellan gum, cellulose, microcrystalline cellulose, xanthan gum, cellulose acetate phthalate, hydropropylcellulose, hydropropylmethylcellulose, ethylcellulose, methylcellulose, L-HPC (low-substituted hydroxypropyl cellulose), carrageenan, croscarmellose, povidone, crospovidone, starch, sodium starch glycolate, glucan, Adjumer® (polyidi[carboxylatophenoxyl[phosphazene), Pleuran (glycan), Pluronic L 121 (Poloxamer401), glyceraldehydes, dihydroxyacetone and combinations thereof; and combination carriers/floss/menstruum, such as without being limited to, directly compressed dried honey (Hony-TAB®), lactose and aspartame, lactose and cellulose, microcrystalline cellulose and carrageenan, microcrystalline cellulose and guar gum, microcrystalline cellulose and sodium carboxymethylcellulose, microcrystalline cellulose and lactose, and a sugar and starch combination.

In some embodiments, the gas-producing component is separately prepared without the API. The API and the gas-producing component can be disposed in the same layer or different layer of a unit dosage form (e.g. a film). In some embodiments, the preparation of the gas-producing component involves mixing the API with the solid matrix material and then subjecting the mixture to conditions of entrapping the gas.

In some embodiments, the gas-producing component includes an acid and a carbonate or bi-carbonate. This carbon dioxide producing component can be used alone or in combination with the gas-trapping component described above. Preferably, the acid and the carbonate or bi-carbonate are disposed in two separate layers. The API and/or permeation enhancer can be on the same layer with either the acid or the carbonate or bi-carbonate. Alternatively, the API and/or permeation enhancer can be disposed in a layer separate from both of the acid or the carbonate or bicarbonate.

The gas-producing effervescent component(s) are also reactive with water to generate and release one or more second gases into the vehicle. Many acidic and basic components are known to react in the presence of water to generate gas. For example, acids, such as citric acid, tartaric acid, malic acid, fumaric acid, adipic acid, succinic acids, and the like, and combinations thereof are reactive with carbonates, or a source thereof, in water to generate CO2 gas. Suitable sources of carbonate include, without limitation, dry solid carbonate, bicarbonate, and sesqui-bicarbonate salts of metals, such as sodium, potassium, lithium, calcium, and magnesium, and ammonium carbonate and bicarbonate. Excess basic component provides advantages, including providing a basic vehicle and/or a basic oral environment, taste masking properties, and many other benefits. In some embodiments, the gas-generating effervescent component accounts for from about 5% to about 90%, from about 15% to about 80%, from about 25% to about 60%, or from about 35% to about 50% of the total weight of the unit dosage form.

Advantages may be gained where the basic component is present in a molar equivalent greater than the acidic component. In some embodiments, the unit dosage form includes the acidic component to basic component ratio in a range from about 1:1 to about 1:10 to provide complete consumption of the acidic component in the gas-generating reaction by reaction with the basic component in the aqueous vehicle. In some embodiments, the unit dosage form includes the acidic component to basic component in a ratio in the range from about 1:2 to 1:7. In some embodiments, the ratio is in the range from about 1:5 to about 1:6. Where the reactive equivalents of the acidic and basic components are equal, the above-disclosed "equivalence" ratios may be used as weight ratios for the amounts of the acidic component(s) relative the basic component(s). For example, an acid with two proton equivalents may be used with sodium carbonate (Na2CO3) in weights (mg or gm amounts) within the ranges above.

Excess basic component also provides additional benefits. For example, the excess may serve to neutralize any acidic components in the vehicle, thereby reducing potential gastrointestinal upset after ingestion of the vehicle. Moreover, basic components generally neutralize saliva (normal saliva has a pH of about 6.5 to about 6.9) and may even provide a basic pH in the oral environment, thereby enhancing absorption of lipophilic medicaments through the oral mucosa. As such, it is herein contemplated that the amounts of acidic and basic components may be adjusted so as to enhance absorption of the medicament(s) into the body, such as through the oral mucosal tissue, sublingual tissue, or buccal tissue.

The unit dosage form may be formulated to optimize exposure of one or both of the gas-producing components to the water content of the vehicle. For example, the formulation may contain a plurality of layers including an outermost layer and a core. Any of the components, including the medicament and the gas-producing component, may be included in the outermost layer or distributed as desired between the outermost layer and the core. Thus, bi-layered or multi-layered tablets, pills, film and the like formulations are contemplated herein. In one embodiment, the outermost layer includes at least the gas-producing component so that upon exposure to the aqueous vehicle, the component dissolves and "pops" or abruptly releases gas to distribute the core components, including for example the medicament and/or the other effervescent component (containing an acid and a carbonate or bicarbonate), throughout the vehicle as they are released. In another embodiment, the outermost layer includes the gas-producing effervescent component (containing an acid and a carbonate or bicarbonate) so as to initiate effervescence in the vehicle prior to the "pops" from the gas-producing component.

In some embodiments, the administration of the unit dosage form requires placing the dosage form in the mouth of the subject. In such a case, the subject's saliva or other oral fluid acts as the vehicle in which the effervescence occurs. In the fluids in the subject's mouth, the formulation generally begins to disintegrate commencing the production and/or evolution of gas. Thus, the amount of gas-dispersing and gas-generating effervescent components in the formulation should be effective to provide a "popping" and/or an effervescent sensation in the mouth of the subject. In other words, the subject should be able to perceive a distinct sensation of "fizzing" or bubbling and "popping" as the formulation disintegrates in the mouth. In some embodiments, the amount of effervescent component(s) in each formulation should be provided to generate about 20 cm3 to about 60 cm3 of gas. The "fizzing" sensation substantially enhances the organoleptic effects of the formulation. A "positive" organoleptic sensation is one which is pleasant and/or enjoyable and which can be perceived readily by a normal human being.

The gas-producing effervescent components should be in amounts effective to assist the rapid and complete disintegration of the dosage form in the aqueous vehicle or in the mouth of the subject. By "rapid", it is understood that the formulation should disintegrate in water, in an aqueous vehicle, or even in a subject's mouth in less than about 10 minutes, and desirably between about 30 seconds and about 7 minutes. In one embodiment of the invention, the formulation is a tablet which dissolves in the vehicle or mouth in between about 30 seconds and about 5 minutes. In another embodiment, it dissolves and disperses in less than about 30 seconds. Disintegration time can generally be measured by observing the disintegration time of the tablet in water at about 37° C. The tablet is immersed in the vehicle without forcible agitation. The disintegration time is the time from immersion for substantially complete dispersion of the tablet as determined by visual observation. This method for measuring disintegration times is only one of the many methods for such purpose, as known by those skilled in this art.

The unit dosage form described herein may further include one or more additional excipients or adjuvants, which can be chosen from those known in the art. For example, adjuvants including flavors, diluents, colors, binders, filler, compaction agents, non-effervescent disintegrants, and the like, commonly referred to as excipients, may be included.

Examples of binders which can be used include acacia, tragacanth, gelatin, starch, cellulose materials such as methyl cellulose and sodium carboxy methyl cellulose, alginic acids and salts thereof, magnesium aluminum silicate, polyethylene glycol, guar gum, polysaccharide acids, bentonites, sugars, invert sugars and the like. Binders may be used in an amount up to about 60% by weight and advantageously from about 10% to about 40% by weight of the dosage form.

Non-effervescent disintegrants include starches as corn starch, potato starch and modified starches thereof, sweeteners, clays, such as bentonite, micro-crystalline cellulose, alginates, gums such as agar, guar, locust bean, karaya, pectin and tragacanth. Disintegrants may comprise up to about 20% by weight and advantageously between about 2% and about 10% by weight of the final dosage form. Notable, these binders and disintegrants may already be sufficiently present in other components of the dosage form, such as in the gas-producing solid matrix.

Coloring agents may include titanium dioxide, and dyes suitable for food such as those known as F. D. & C. dyes and natural coloring agents such as grape skin extract, beet red powder, beta-carotene, annatto, carmine, turmeric, paprika, etc. The amount of coloring used may range from about 0.1% to about 3.5% by weight of the unit dosage form.

Flavors incorporated in the unit dosage form may be chosen from synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavors are vanilla, citrus oil, including lemon, orange, grape, lime and grapefruit, and fruit essences, including apple pear, peach, strawberry, raspberry, cherry, plum, pineapple, apricot and so forth. Flavors, which have been found to be particularly useful, include commercially available orange, grape, cherry and bubble gum flavors and mixtures thereof. The amount of flavoring may depend on a number of factors, including the organoleptic effect desired. Flavors may be present in an amount ranging from about 0.5% to about 3.0% by weight of the unit dosage form. Commonly accepted flavors include grape and cherry flavors, and citrus flavors such as orange. It is also appreciated that inclusion of flavoring agents can also influence the final flavor of the vehicle, furthering compliance with ingestion of the API/medicament.

A bioadhesive, such as a bioadhesive polymer, may be included in the unit dosage form to increase the contact time between the dosage form and the oral mucosa, particularly where the dosage form is administered directly into the oral cavity and the vehicle is saliva. Non-limiting examples of known bioadhesives, or mucoadhesives, include carbopol (various grades), sodium carboxy methylcellulose, methylcellulose, polycarbophil (Noveon AA-1), hydroxypropyl methylcellulose, hydroxypropyl cellulose, sodium alginate, and sodium hyaluronate.

The individual components are formulated into a solid effervescent formulation for placement in an aqueous vehicle. Suitable solid formulations include, without limitation, orally dispersable pills, chewable pills, buccal adhesive pills, tablets, capsules including hard an soft-shelled gelatin capsules, granular powder, troches, and dragees. These formulations may be prepared by techniques known in the art. For example, a pill may be manufactured by well-known pill manufacturing procedures Tablets may be manufactured by well-known tableting procedures. In common tableting processes, materials to be tableted are deposited into a cavity, and one or more punch members are then advanced into the cavity and brought into intimate contact with the materials to be pressed, whereupon compressive force is applied. The materials are thus forced into conformity with the shape of the punches and the cavity. Hundreds, and even thousands, of tablets per minute can be produced in this fashion. Various tableting methods, well known to those skilled in the art, are comprehensively discussed in Lieberman, Pharmaceutical Dosage Form: Tablets, Vol. 1, 2nd Ed., pp 372-376, New York, 1989, which disclosure is incorporated herein by reference in its entirety.

Known granulation and wet-granulation methods for forming tablets may be utilized. Granulation generally includes any process of size enlargement whereby small particles are gathered together into larger, permanent aggregates to yield a free-flowing composition having a consistency suitable for tableting. Such granulated compositions may have consistency similar to that of dry sand. Granulation may be accomplished by agitation in mixing equipment or by compaction, extrusion or globulation. Granulation also includes, for example, a process where a liquid form of a material is rendered granular, or in a solid form, by combining it with a granular core material, such as a sugar particle. Such granular material may be produced, for example, by spray-drying the liquid onto the core particle. Thus, individual materials maybe granulated to lend themselves to tableting.

Lubricants are normally used in manufacture of effervescent tablets. Without the use of an effective lubricant, tableting by use of high-speed equipment may be difficult. The term “lubricant” as used herein, means a material which can reduce the friction arising at the interface of the tablet and the die wall during compression and ejection thereof. Lubricants may also serve to prevent sticking to the punch and, to a lesser extent, the die wall as well. Lubricants, suitable for the unit dosage form, may be used in an amount of up to 1.5% by weight, and advantageously between about 0.5% and about 1.0% by weight of the total composition.

Extrinsic or intrinsic lubricants may be incorporated in the material to be tableted. A lubricant which is directly applied to the tableting tool surface in the form of a film, as by spraying onto the die cavity and/or punch surfaces, is known as an extrinsic lubricant. Although extrinsic lubricants can provide effective lubrication, their use requires complex application equipment and methods which add cost and reduce productivity. Magnesium, calcium and zinc salts of stearic acid have long been regarded as the most efficient intrinsic lubricants in common use. Concentrations of 1% or less by weight are usually effective.

Another aspect of this patent document provides a method of making the unit dosage form descried herein. The method generally includes mixing a therapeutically effective amount of the API with a permeation enhancer into a suitable form. The permeation enhancer includes one or more components, each in a predetermined amount as described above.

The permeation enhancer is in an effective amount to enhance the penetration of the API of the unit dosage form through oral mucosa. The permeation enhancer comprises at least one of the following:

(a) an oleic acid derived surfactant, wherein the permeation enhancer has a HLB value ranging from about 7 to about 12; and (b) a gas-producing component.

Another aspect of this patent document provides a method of treating a disease in a subject, comprising administration of a unit dosage form described herein in an amount effective to treat the disease. The disease is selected from the group consisting of Parkinson’s disease, erectile dysfunction, Alzheimer’s disease, asthma, diarrhea, and migraine headache.

The unit dosage form can be placed in or near the sublingual mucosa or the buccal mucosa of the subject’s mouth. In some embodiments, the unit dosage form contains polymers that provide mucoadhesive properties to the unit dosage form such as a film. The time period for which it is desired to maintain the film in contact with the mucosal tissue depends on the type of active contained in the dosage form. Some actives may only require a few minutes for delivery through the mucosal tissue, whereas other actives may require up to several hours or even longer. Accordingly, in some embodiments, one or more water-soluble polymers may be used to form the film. In other embodiments, however, it may be desirable to use combinations of water-soluble polymers and polymers that are water-swellable, water-insoluble and/or biodegradable. The inclusion of one or more polymers that are water-swellable, water-insoluble and/or biodegradable may provide films with slower dissolution or disintegration rates than films formed from water-soluble polymers alone. As such, the film may adhere to the mucosal tissue for longer periods or time, such as up to several hours, which may be desirable for delivery of certain active components.

The amount of the API included in the unit dosage form will generally depend upon the particular API or medicament, its intended use, and patient profile. The amount is generally selected in accordance with known principles of pharmacy. Effective amounts are generally that amount or quantity of an API, which is sufficient to elicit the required or desired therapeutic response (biological response) when administered to a patient. In some embodiments, the unit dosage form includes the API in amounts of up to about 1000 mg. In some embodiments, the unit dosage form includes the API/medicament(s) in amounts ranging from about 25 mg to about 100 mg. In some embodiments, the unit dosage form includes the API/medicament(s) in amounts of up to about 25 mg.

In some embodiments, the method further includes administering a second agent selected from the group consisting of antihistamines, medications treat respiratory disorders, antiemetics, sleep aids, medications to treat diarrhea, oral hygiene agents, migraine treatments, CNS medicines, and first-aid medications.

EXAMPLES

Example 1

General procedures for manufacturing oral thin films: a coating solution was prepared by adding aqueous water solution into a homogeneous mixture of ingredients (see for example Table 1). The resulting mixture contained a solid content of approximately 20-80% depending on the viscosity of the mixture. The coating mixture mass was degassed in a vacuum mixer, coated on a polyester film, and dried in a hot air circulating oven at 40-100° C. to form a thin film. The film was then cut into dosage units ready for packaging.

TABLE 1

| Caffeine Oral Thin Film (OTF) Formulations | | | | | | |
|---|---|---|---|---|---|---|
| Dry film weight (mg) | CF28A | CF28B-M1944 | CF28B&PR | CF219-TW | CF219TW-Bicarbonate | CF214-Bicarbonate |
| Caffeine (mg) | 25 | 25 | 25 | 25 | 25 | 25 |
| Labrafil M1944 CS (HLB9.0) | | 5 | 5 | | | 5 |
| Tween 80 (HLB15) | | | | 5 | 5 | |
| Glycerin | 10 | 10 | 10 | 10 | 10 | 10 |
| Pullulan | 64.5 | 59.5 | 49.5 | 49.5 | 52.5 | 45.5 |
| Sodium bicarbonate | | | | | 9 | 9 |
| Citric acid | | | | | 3 | 3 |
| Sucralose | 0.5 | 0.5 | 0.5 | 0.5 | 0.5 | 0.5 |
| Grinded pop-rocks | | | 100.0 | | | |
| FD&C Yellow | 0.03 | 0.03 | 0.03 | 0.03 | 0.03 | 0.03 |

Note: the film formulations of CF219TW-Bicarbonate and CF214-Bicarbonate do not contain citric acid, which was separately added to the test device. Labrafil M1944 CS (HLB value of 9.0) is commercially available from Gattefosse. Commercially available pop—was grinded into particles for incorporation into the film.

A dual layer film formulation was prepared. Each of the layer was separately prepared according to the above mentioned process. The two layers of 214A and 214B were then laminated to form a prototype CF214.

TABLE 2

| Dual Layer Film Formulation | | | |
|---|---|---|---|
| | CF214A-Layer1 | | CF214B-Layer2 |
| Caffeine | 10 | Glycerin | 8 |
| Glycerin | 4 | Pullulan | 22 |
| PM1944 | 2 | Na Bicarbonate particles | 20 |
| Pullulan | 21.78 | Blue color | 0.02 |
| Sucralose | 0.2 | SUM | 40 |
| Citric Acid | 5 | | |
| FD&C Yellow | 0.02 | | |
| SUM | 43 | | |

Methods of Testing Permeation

Various methods can be used for testing the film formulations described herein. The following methods are described as examples.

Franz Diffusion System Method: Franz Diffusion System is the most widely used in vitro method to study oral mucosal permeability across the mucosa. It tests drug permeation across isolated tissue mounted in permeability chambers. Researchers use animal buccal tissues and synthetic membrane (nylon, etc.) extensively for the in vitro drug permeability studies in this method. The polymeric membranes are usually used for in vitro release testing (IVRT). According to the FDA SUPAC-SS (May 1997), any appropriate inert and commercially available synthetic membranes can be used. Usually hydrophilic polymeric membranes with a pore size of 0.45 μm are used. The testing generally includes the following steps:

1. Fill Franz Cell receiving chamber with PBS or water solution (5 ml) and stir with magnetic bar.
2. Cover the surface using a nylon membrane with a diameter of 25 mm and a pore size of 0.45 μm.
3. Place the oral thin film in the center of the membrane and secure the donating chamber onto the receiving chamber, which effectively sandwiches the oral film and membrane between the two chambers.
4. Add any other ingredients (pop rocks) if any, into the donating chamber. Add 1 ml of water solution into the donating chamber.
5. Collect 0.15 mL samples from the receiving chamber and refill the solution at 15 min, 40 min, 1 hour, 2 hours, 3 hours, and 4 hours.

Buccal Epithelial Cell Cultures: Cultured human buccal epithelium model (such as EpiOral™) consists of normal human keratinocytes cultured to form a 3D differentiated tissue that histologically and biochemically resembles human buccal tissue. This model offers good similarity to human buccal mucosa in terms of structures, protein expression and lipid content. A good correlation between the permeation of fentanyl across cultured buccal epithelium, applied in different tablet formulations, and bioavailability in human has been observed.

Buccal absorption test: One of the simplest measurements of drug penetration through oral mucosal tissue is a buccal absorption test called as the "swirl and spit test" (Beckett and Triffs). In this method, a buffered drug solution was placed in the subject's mouth and was swirled in the mouth for a period of time. The solution was the expelled and analyzed. This method was modified to study penetration of the oral thin film of caffeine formulated with different penetration enhancers. More details on this method is provided at J. Pharm Pharmacol, 1967, 19(Suppl.): 31S-41S. 63.

Permeation through buccal mucosa is considered to be a passive diffusion process. The release profile of drug was determined over time and plotted based upon total amount of drug loaded as the cumulative amount of loaded drug released versus time (Fick's law) or square root of time as suggested by Higuchi. Parameters relating to permeation such as permeability coefficient (P under Fick's law (cm/hr)) and Higuchi dissolution constant ($K_H$ under Higuchi equation ($mg/cm^2/h^{1/2}$)) can be calculated with known methods equations.

Figure 2:
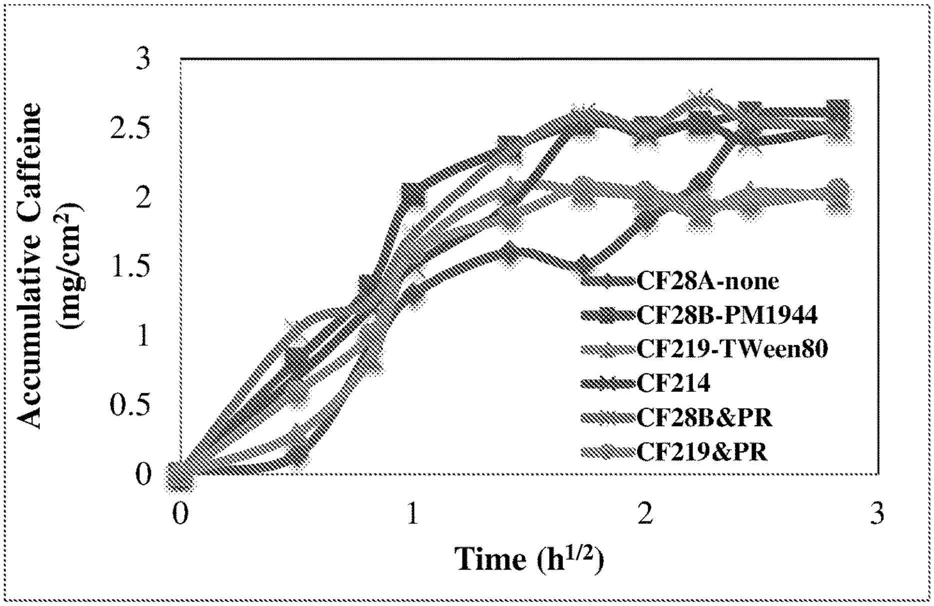
FIG. 2 shows in vitro release of caffein from an exemplified oral film (x axis defined as $t^{1/2}$).

FIGS. 1 and 2 show the amount of accumulative caffeine at different time points. Table 3 shows the permeability coefficients of caffeine diffusing through Nylon membrane for the tested oral-thin films.

TABLE 3

| Permeability coefficients of caffeine from different oral-thin films using the Franz Cell Diffusion System. | | | | | | |
|---|---|---|---|---|---|---|
| | CF28A-none | CF28B-PM1944 | CF219-TWeen80 | CF214 (effervescent) | CF28B & PR* | CF219 & PR* |
| Permeability Coefficient (cm/h), 1 hour | 1.22 | 1.67 | 1.67 | 1.27 | 1.33 | 1.60 |
| Permeability Coefficient (PC, cm/h), 15 min | 0.49 | 2.90 | 1.25 | 2.48 | 3.66 | 2.53 |

The Franz Cell release rates of drug through membranes, derived from the Higuchi equation:

Caffeine is highly hydrophilic. In the above test using Nylon membrane, an equilibrium was achieved within 3 hours. As gas-producing component of the film released vigorously high-pressured gas within a short period of time, its impact on the drug penetration can be best interpreted by the permeation coefficient at 15 minutes. The penetration coefficient was 2.90 and 3.66, for the formula CF28B without and with gas-producing component in the Franz Cell donating chamber, respectively. It was 1.25 and 2.53 for the formula CF219 without or with addition of gas-producing component into the system. This suggest that the penetration of caffeine through a Nylon membrane was enhanced by addition of the gas-producing component. Labrafil M1944 CS enhanced caffeine penetration through Nylon membrane 40% higher (PC-1 hour of CF28B (1.22) & CF28A (1.67), KH of CF28B (1.04) & CF28A (1.67)).

TWEEN 80/PEG-20 sorbitan monooleate has a HLB of 15.0. It was demonstrated that Tween 80 enhanced caffeine penetration through Nylon membrane by 30%-40%.

The Caffeine film CF214 contained citric acid and sodium bicarbonate which are identified as effervescent agents. They increased the penetration of caffeine through the Nylon membrane.

Example 2

The “swirl and spit test” (Beckett and Triffs 1968) was modified to evaluate sublingual absorption of caffeine sublingual film prototypes. In this method, the caffeine sublingual film was placed under the tongue and held for 2 minutes. The subjects were refrained from swallowing during this period of time. After dosing for 2 minutes, rinse mouth 3 times, each time with 20 ml of water swirling inside mouth 20-30 times for 1 minute. Collect all washing solutions and assay.

Each study film was cut into 1 inch by 1 inch and weighed approximately 40 mg with caffeine loading of 10 mg. Sublingual absorption (%) was estimated and tabulated below.

TABLE 4

| Sublingual absorption test of caffeine sublingual oral thin films | | | | | |
|---|---|---|---|---|---|
| Formulation | CF28A | CF28A &PR* | CF28B | CF28B &PR* | CF214 |
| Sublingual absorption of caffeine thin film after dosing for 2 minutes | 18.8% | 30.9% | 21.8% | 34.6% | 27.2% |

*PR = gas-producing particles (100 mg)

This test indicated that gas-producing component increased caffeine buccal/sublingual absorption. Effervescent agents (citric acid and sodium bicarbonate) also increased caffeine buccal/sublingual absorption.

Example 4

An organ thin film containing apomorphine hydrochloride was prepared for testing of diffusion through nylon membrane and buccal tissue permeation. The preparation of donor solution involves apomorphine hydrochloride at a concentration of 0.5 mg/ml and an enhancer at a concentration of 0.1 mg/ml. Cultivated EpiOral tissues were used as the buccal tissue model to evaluate apomorphine absorption through buccal mucosal. The drug absorption protocol from MatTek, with some modifications, was utilized to study the permeability of apomorphine under different study conditions such as types of enhancers and concentrations of polymers.

TABLE 5

| apomorphine oral thin film formulation | | |
|---|---|---|
| Apomorphine OTF Formulation | APO6B | APO6A |
| API (Apomorphine HCL) | 40.0% | 40.00% |
| Labrafil M 1944 | 0.0% | 12.00% |
| Glycerin | 0.0% | 8.00% |
| Pullulan | 48.46% | 28.46% |
| PVA Mix | 10.00% | 10.00% |
| BHA, USP | 1.00% | 1.00% |
| Sucralose | 0.50% | 0.50% |
| FD&C Blue #1 | 0.04% | 0.04% |
| SUM | 100.00% | 100.00% |

Figure 3:
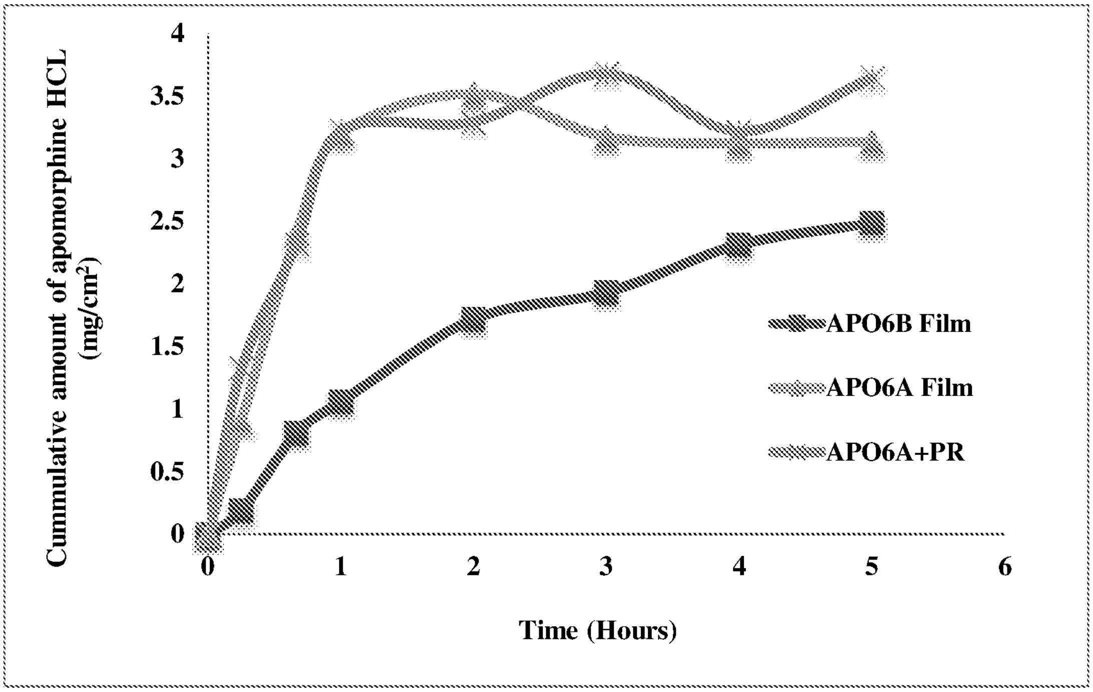
FIG. 3 illustrates in vitro release of apomorphine from an exemplified oral thin film over a period of 5 hours.
Figure 4:
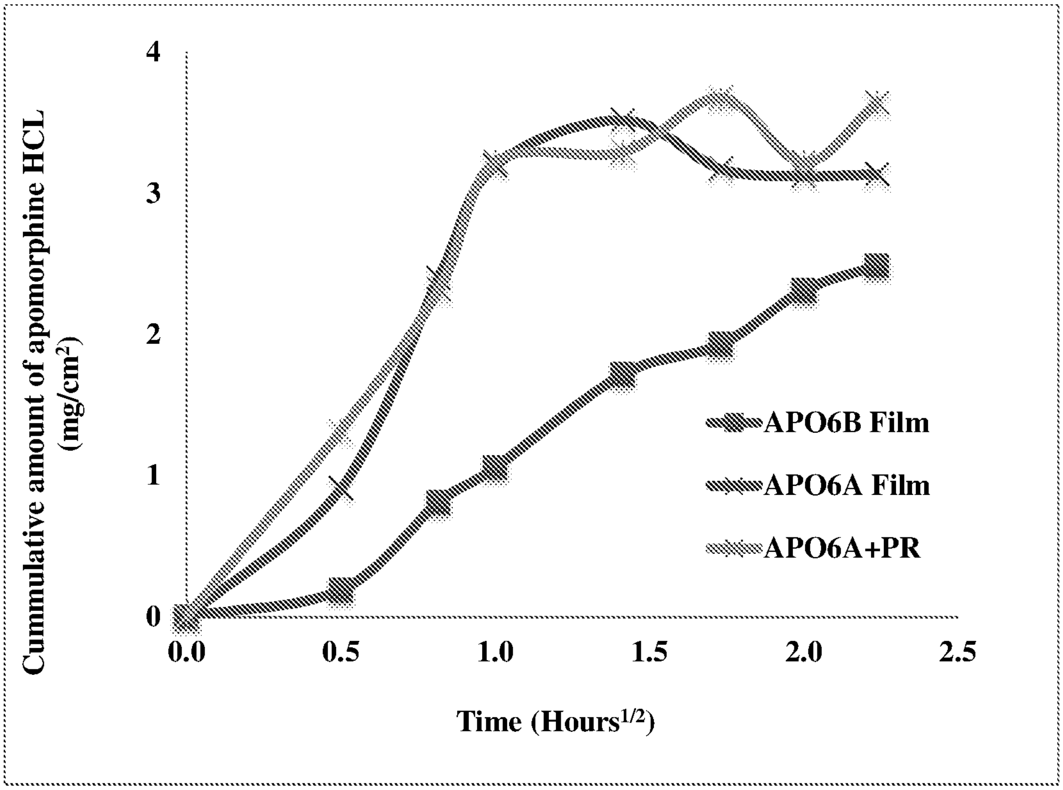
FIG. 4 illustrates in vitro release of apomorphine from an exemplified oral thin film over a period of 2.5 hours.

FIGS. 3 and 4 show the in vitro release of apomorphine at different time points. The two apomorphine oral thin film prototypes are different. APO6B contains no penetration enhancers while APO6A contains Labrafil M 1944. Labrafil M1944 CS is chemically (commercially labeled as Oleoyl Polyoxyl-6 glycerides NF) has a HLB value of 9.0. The permeation coefficients of APO6B and APO6A are 0.62 and 1.72, respectively. The Higuchi dissolution constant of APO6B and APO6A are 1.08 and 3.20, respectively. Both parameters suggest a-tripled penetration effect of APO6A due to addition of Labrafil M 1944.

As gas-producing component releases vigorously high-pressured gas within a short period of time, its impact on the drug penetration can be best interpreted by the permeation coefficient at 15 minutes. Penetration of apomorphine through a Nylon membrane was enhanced (a penetration coefficient –15 min increases 46% from 1.87 to 2.73) for APO6A formulation without or with gas-producing component.

TABLE 6

Permeability coefficients of apomorphine diffusing through Nylon membrane

| | APO6B (no enhancers) | APO6A (With enhancer Labrafil M 1944) | APO6A&PR* |
|---|---|---|---|
| Permeability Coefficient (cm/h), 1 hour | 0.62 | 1.72 | 1.59 |
| Permeability Coefficient (cm/h), at first time point when APO becomes detectable | 0.41 | 1.87 | 2.73 |

The Franz Cell release rates of drug through membranes, derived from the Higuchi equation:

| | APO6B | APO6A | APO6A&PR |
|---|---|---|---|
| $K_H$, Higuchi dissolution constant ($mg/cm^2/h^{1/2}$), 3 hours | 1.08 | 3.20 | 3.20 |

Labrafil M1944 CS (HLB: 9.0) resulted in highest penetration enhancement (25% higher than the control solution without any enhancer added). By contrast, Mono-Di-Glyceride with a HLB value of 3.0 results in a hindering penetration of apomorphine rather than enhancing penetration. Other enhancers, with HLB values ranging between 8.6 and 15, improved the buccal absorption of apomorphine by 10-20%.

Table 7 and Table 8 show additional unit dosage forms of Apomorphine.

TABLE 7

Apomorphine Oral Thin Film (OTF) Formulations

| Dry film (mg) | Formula #A | Formula #B | Formula #C | Formula #D | Formula #E | Formula #F | Formula #G |
|---|---|---|---|---|---|---|---|
| API (Apomorphine HCL), mg | 30 | 30 | 30 | 30 | 30 | 30 | 30 |
| SPAN 20 (HLB8.6) | | 10 | | | 10 | | 2 |
| Labrafil M1944 CS (HLB9.0) | 15 | | | 15 | | | 3 |
| Tween 80 (HLB15) | | 5 | | | 5 | 10 | |
| Glycerin | | | 10 | | | | 10 |
| Pullulan | 17.6 | 29.6 | 34.6 | 17.5 | 25.57 | 31.6 | 17.5 |
| PVA 40-88 | 7.5 | | | 5.5 | | | 5.5 |
| PVA 18-88 | 4.5 | | | 4.5 | | | 4.5 |
| Sucralose | 0.4 | 0.4 | 0.4 | 0.4 | 0.4 | 0.4 | 0.375 |
| Butylated hydroxyanisole (BHA), NF (Antioxidant) | | | | 2.0 | 2 | 1 | 2 |
| Benzyl Alcohol, NF (Preservative) | | | | | 1 | 1 | |
| EDTA, Disodium ethylenediaminetetraacetic acid dihydrate (Chelating agent) | | | | 0.5 | 0.5 | 0.5 | 0.5 |
| FD&C Blue #1 | 0.03 | 0.030 | 0.03 | 0.03 | 0.03 | 0.03 | 0.03 |
| SUM (mg) | 75 | 75 | 75 | 75 | 75 | 75 | 75 |

TABLE 8

| Apomorphine Oral Thin Film (OTF) Formulations | | | | | | | |
|---|---|---|---|---|---|---|---|
| Dry film weight (mg) | Formula #A2 | Formula #B2 | Formula #C2 | Formula #D2 | Formula #E2 | Formula #F2 | Formula #G2 |
| API (Apomorphine HCL), mg | 30 | 30 | 30 | 30 | 30 | 30 | 30 |
| SPAN 20 (HLB8.6) | | 5 | | 7.5 | 5 | | 3 |
| Labrafil M1944 CS (HLB9.0) | 10 | 5 | 5 | 2.5 | | 2.5 | 5 |
| Tween 80 (HLB15) | | 5 | | | 5 | 5 | 7 |
| Glycerin | 5 | | 5 | | 5 | 2.5 | |
| Pullulan | 17.6 | 29.6 | 34.6 | 17.0 | 26.07 | 32.1 | 17 |
| PVA 40-88 | 7.5 | | | 5.5 | | | 5.5 |
| PVA 18-88 | 4.5 | | | 4.5 | | | 4.5 |
| Sucralose | 0.4 | 0.4 | 0.4 | 0.4 | 0.4 | 0.4 | 0.375 |
| Na Metabisulfite, NF (Antioxidant) | | | | 2.0 | 2 | 1 | 2 |
| Benzyl Alcohol, NF (Preservative) | | | | | 1 | 1 | |
| EDTA, Disodium ethylenediaminetetraacetic acid dihydrate (Chelating agent) | | | | 0.5 | 0.5 | 0.5 | 0.5 |
| FD&C Blue #1 | 0.03 | 0.030 | 0.03 | 0.03 | 0.03 | 0.03 | 0.03 |
| SUM (mg) | 75 | 75 | 75 | 75 | 75 | 75 | 75 |

Example 5

The HLB values of common surfactants are published in the literature, including Shinoda, et al., Emulsions and Solubilization, John Wiley and Sons, New York (1986); Nollet, et al., International Journal of Cosmetic Science, 2019, 41, 99-108, the entire disclosure of these references are hereby incorporated by reference. For agents such as PEG6 monooleate and PEG6 dioleate without reported HLB value in the references, calculation based on Griffins Method can be used. Griffins Method: HLB=20*(mass of hydrophilic part/total molecular mass)).

Exemplary surfactants with known HLB value are shown in Table 9 below.

TABLE 9

| HLB values for Surfactants | |
|---|---|
| Surface Active Agents | HLB |
| Oleic acid | 1.0 |
| Polyoxyethylene sorbitol wax derivative (G-1706) | 2.0 |
| Sorbitan tristearate | |
| Glyceryl monostearate | 2.1 |
| Sorbitan mono-oleate (Span 80) | 3.8 |
| Diethylene glycol monostearate | 4.3 |
| Glyceryl monostearate (Tegin) | 4.7 |
| Diethylene glycol monolaurate | 5.5 |
| Sorbitan monolaurate (Span 20) | 6.1 |
| Polyethylene lauryl ether (Brij 30) | 8.6 |
| Jelatin (Pharmagel B) | 9.5 |
| Methyl cellulose (Methocel 15 cP) | 9.8 |
| Polyoxyethylene lauryl ether (G-3705) | 10.5 |
| Polyoxyethylene monostearate (Myrj 45) | 10.8 |
| Triethanolamine oleate | 11.1 |
| Polyoxyethylene alkyl phenol (Igepal Ca-630) | 12.0 |
| Polyethylene glycol 400 monolaurate | 12.8 |
| Polyoxyethylene sorbitan mono-oleate | 13.1 |
| (Tween 80) | 15.0 |
| Polyoxyethylene sorbitan monolaurate | |
| (Tween 20) | 16.7 |
| Polyoxyethylene lauryl ether (Brij 35) | |

TABLE 9-continued

| HLB values for Surfactants | |
|---|---|
| Surface Active Agents | HLB |
| Sodium oleate | 16.9 |
| Potassium oleate | 18.0 |
| Sodium lauryl sulphate | 20.0 |
| | 40.0 |

The HLB value of a mixture of two components (weight concentrations of x and y, HLB values of HLB1 and HLB2, respectively) can be estimated as $$\text{HLB value of mixture} = x^{*}\text{HLB1} + y^{*}\text{HLB2}$$

TABLE 10

| HLB values of different combinations of glycerides, polyoxyglycerides, oleic acid and derivative surfactants. | | | |
|---|---|---|---|
| | HLB | Concentration | Mixture HLB |
| Glyceryl monooleate | 3.4 | 25% | 5.9625 |
| Glyceryl dioleate | 1.8 | 25% | |
| PEG6 monooleate | 11.0 | 25% | |
| PEG6 dioleate | 7.6 | 25% | |
| Glyceryl monooleate | 3.4 | 50% | 2.6 |
| Glyceryl dioleate | 1.8 | 50% | |
| PEG6 monooleate | 11.0 | 0% | |
| PEG6 dioleate | 7.6 | 0% | |
| Glyceryl monooleate | 3.4 | 50% | 7.22 |
| Glyceryl dioleate | 1.8 | 0% | |
| PEG6 monooleate | 11.0 | 50% | |
| PEG6 dioleate | 7.6 | 0% | |
| Glyceryl monooleate | 3.4 | 40% | 7.984 |
| Glyceryl dioleate | 1.8 | 0% | |
| PEG6 monooleate | 11.0 | 60% | |
| PEG6 dioleate | 7.6 | 0% | |
| Glyceryl monooleate | 3.4 | 25% | 8.206 |
| Glyceryl dioleate | 1.8 | 10% | |
| PEG6 monooleate | 11.0 | 65% | |
| PEG6 dioleate | 7.6 | 0% | |
| Glyceryl monooleate | 3.4 | 10% | 8.904 |
| Glyceryl dioleate | 1.8 | 0% | |
| PEG6 monooleate | 11.0 | 50% | |

TABLE 10-continued

HLB values of different combinations of glycerides, polyoxyglycerides, oleic acid and derivative surfactants.

| | HLB | Concentration | Mixture HLB |
|---|---|---|---|
| PEG6 dioleate | 7.6 | 40% | |
| Glyceryl monooleate | 3.4 | 0% | 9.325 |
| Glyceryl dioleate | 1.8 | 0% | |
| PEG6 monooleate | 11.0 | 50% | |
| PEG6 dioleate | 7.6 | 50% | |
| Glyceryl monooleate | 3.4 | 0% | 10.354 |
| Glyceryl dioleate | 1.8 | 0% | |
| PEG6 monooleate | 11.0 | 80% | |
| PEG6 dioleate | 7.6 | 20% | |
| Oleic Acid | 1 | 0% | 15 |
| Span 80 (sorbitan monooleate) | 4.3 | 0% | |
| Tween 80 (polyoxyethylene sorbitan monooleate) | 15 | 100% | |
| Oleic Acid | 1 | 0% | 15 |
| Span 80 | 4.3 | 0% | |
| Tween 80 | 15 | 100% | |
| Oleic Acid | 1 | 25% | 11.5 |
| Span 80 | 4.3 | 0% | |
| Tween 80 | 15 | 75% | |
| Oleic Acid | 1 | 30% | 10.8 |
| Span 80 | 4.3 | 0% | |
| Tween 80 | 15 | 70% | |
| Oleic Acid | 1 | 50% | 8 |
| Span 80 | 4.3 | 0% | |
| Tween 80 | 15 | 50% | |
| Oleic Acid | 1 | 0% | 9.65 |
| Span 80 | 4.3 | 50% | |
| Tween 80 | 15 | 50% | |
| Oleic Acid | 1 | 0% | 8.58 |
| Span 80 | 4.3 | 60% | |
| Tween 80 | 15 | 40% | |
| Oleic Acid | 1 | 0% | 7.51 |
| Span 80 | 4.3 | 70% | |
| Tween 80 | 15 | 30% | |

It will be appreciated by persons skilled in the art that invention described herein are not limited to what has been particularly shown and described. Rather, the scope of the invention is defined by the claims which follow. It should further be understood that the above description is only representative of illustrative examples of embodiments. The description has not attempted to exhaustively enumerate all possible variations. The alternate embodiments may not have been presented for a specific component of the dosage form or a step of the method, and may result from a different combination of described excipient or agent, or that other un-described alternate embodiments may be available for a dosage form or method, is not to be considered a disclaimer of those alternate embodiments. It will be appreciated that many of those un-described embodiments are within the literal scope of the following claims, and others are equivalent.

The invention claimed is:

1. A unit dosage form formulated for oral transmucosal delivery of an active pharmaceutical ingredient (API), comprising:

a therapeutically effective amount of the API and a permeation enhancer, wherein the permeation enhancer is in an effective amount to enhance the penetration of the API of the unit dosage form through oral mucosa, and wherein the permeation enhancer comprises polyoxytheylene sorbitan monooleate and oleic acid, wherein the permeation enhancer has a HLB value ranging from about 8 to about 11, wherein the API is octreotide or oxytocin.

2. The unit dosage form of claim 1, wherein the API ranges from about 5 mg to about 40 mg.

3. The unit dosage form of claim 1, wherein the permeation enhancer consists of oleic acid and polyoxyethylene sorbitan monooleate.

4. The unit dosage form of claim 1, wherein the API and the permeation enhancer are in a ratio ranging from about 5:1 to about 1:2 by weight.

5. The unit dosage form of claim 1, wherein the API and the permeation enhancer are in a single layer film.

6. The unit dosage form of claim 1, wherein the API is oxytocin.

* * * * *